(12) United States Patent
Beaufore et al.

(10) Patent No.: US 7,037,303 B2
(45) Date of Patent: May 2, 2006

(54) URINARY FLOW CONTROL VALVE (75) Inventors: Spencer W. Beaufore, Dublin, OH (US); Glenn D. Brunner, Dublin, OH (US)

(73) Assignee: Opticon Medical, Inc., Dublin, OH (US)

( * ) Notice: Subject to any disclaimer, the term of this patent is extended or adjusted under 35 U.S.C. 154(b) by 719 days.

(21) Appl. No.: 10/000,276

(22) Filed: Nov. 2, 2001

(65) Prior Publication Data
US 2003/0009079 A1 Jan. 9, 2003

Related U.S. Application Data (60) Provisional application No. 60/303,694, filed on Jul. 6, 2001.

(51) Int. Cl.
| | |
|---|---|
| A61M 25/16 | (2006.01) |
| A61M 25/18 | (2006.01) |
| A61M 5/00 | (2006.01) |
| F16K 15/14 | (2006.01) |
| F16K 31/00 | (2006.01) |

(52) U.S. Cl. .......... 604/537; 604/34; 604/167.04; 604/236; 604/247; 604/323; 604/335; 251/336; 251/342; 137/849

(58) Field of Classification Search .......... 604/34, 604/167.04, 236, 247, 537, 544, 323, 335, 604/350; 251/336, 342; 137/843, 844, 846, 137/847, 849
See application file for complete search history.

(56) References Cited

U.S. PATENT DOCUMENTS

| | | | |
|---|---|---|---|
| 1,281,974 A | 10/1918 | Kaeding | 137/232 |
| 2,064,695 A | 12/1936 | Sipe | 137/847 |
| 2,328,948 A | 9/1943 | Bourke | 217/103 |
| 2,446,571 A | 8/1948 | Browne | 137/847 |
| 2,710,623 A | 6/1955 | Kolos | 137/223 |
| 2,755,060 A | 7/1956 | Twyman | 251/342 |
| 2,959,359 A | 11/1960 | Casaletto | 239/455 |
| 3,066,767 A | 12/1962 | Djordjevitch | 188/320 |
| 3,079,940 A | 3/1963 | Keefe | 137/223 |
| 3,148,696 A | 9/1964 | Hoke | 137/318 |
| 3,167,089 A | 1/1965 | Gordon | 137/517 |
| 3,298,370 A | 1/1967 | Beatty | 604/350 |
| 3,320,972 A | 5/1967 | High et al. | 137/844 |
| 3,387,624 A | 6/1968 | Soucy | 137/847 |
| 3,421,509 A | 1/1969 | Fiore | |
| 3,504,699 A | 4/1970 | Grise | 137/846 |
| 3,517,682 A | 6/1970 | Smith | 137/68.23 |
| 3,565,106 A | 2/1971 | Baumbach | 137/513.3 |

(Continued)

OTHER PUBLICATIONS

International Search Report for PCT/US03/00719, mailed May 7, 2003 (2 pages).

*Primary Examiner*—Tatyana Zalukaeva
*Assistant Examiner*—Michael G. Bogart
(74) *Attorney, Agent, or Firm*—Wood, Herron & Evans, LLP (57) ABSTRACT

A flow control valve (22) such as for a catheter (10) allows discharge of urine from a bladder (12) by manual actuation. The valve (22) may be a double-duckbill valve (22) with a single slit (62) at one apex (60a) thereof. An elastomeric band (66) is positioned in a groove (68) of the valve member (22). An isolation member such as a stem (72) spaces the valve (22) from the walls (34, 36) of the valve housing (32). Crush limiting structure, such as a tube (76) or blade (82), is provided within valve member (22), or stop elements (86 or 92) are positioned external to valve member (22).

92 Claims, 6 Drawing Sheets

U.S. PATENT DOCUMENTS

| | | | |
|---|---|---|---|
| 3,566,964 A | 3/1971 | Livingston | 166/224 |
| 3,773,233 A | 11/1973 | Souza | 222/490 |
| 3,822,720 A | 7/1974 | Souza | 137/525.1 |
| 3,858,604 A | 1/1975 | Bender, Jr. et al. | 137/488 |
| 3,861,416 A | 1/1975 | Wichterle | 137/525.3 |
| 3,896,849 A | 7/1975 | Ervin et al. | 137/525.1 |
| 3,967,645 A | 7/1976 | Gregory | 137/525.1 |
| 4,030,142 A | 6/1977 | Wolfe | 3/1.5 |
| 4,143,853 A | 3/1979 | Abramson | 251/149.1 |
| 4,177,814 A | 12/1979 | Knepshield et al. | 128/348 |
| 4,222,126 A | 9/1980 | Boretos et al. | 3/1.5 |
| 4,341,239 A | 7/1982 | Atkinson | 137/493 |
| 4,364,127 A | 12/1982 | Pierce et al. | 3/1.5 |
| 4,375,864 A | 3/1983 | Savage | 222/81 |
| 4,424,833 A | 1/1984 | Spector et al. | 137/849 |
| 4,434,810 A | 3/1984 | Atkinson | 137/493 |
| 4,436,519 A | 3/1984 | O'Neill | 604/175 |
| 4,465,102 A | 8/1984 | Rupp | 137/849 |
| 4,475,548 A | 10/1984 | Muto | 128/207.14 |
| 4,524,805 A | 6/1985 | Hoffman | 137/846 |
| 4,535,818 A | 8/1985 | Duncan et al. | 137/846 |
| 4,535,819 A | 8/1985 | Atkinson et al. | 137/846 |
| 4,566,493 A | 1/1986 | Edwards et al. | 137/846 |
| 4,612,960 A | 9/1986 | Edwards et al. | 137/846 |
| 4,673,393 A | 6/1987 | Suzuki et al. | 604/167 |
| 4,685,840 A * | 8/1987 | Wolff | 406/47 |
| 4,725,266 A | 2/1988 | Siposs | 604/119 |
| 4,758,224 A | 7/1988 | Siposs | 604/119 |
| 4,765,588 A | 8/1988 | Atkinson | 251/149.1 |
| 4,798,594 A | 1/1989 | Hillstead | 604/167 |
| 4,809,679 A | 3/1989 | Shimonaka et al. | 128/4 |
| 4,846,836 A | 7/1989 | Reich | 623/11 |
| 4,861,331 A | 8/1989 | East et al. | 604/9 |
| 4,924,923 A | 5/1990 | Boehmer et al. | 141/312 |
| 4,932,938 A | 6/1990 | Goldberg et al. | 604/96 |
| 4,946,449 A | 8/1990 | Davis, Jr. | |
| 4,960,412 A | 10/1990 | Fink | 604/167 |
| 4,968,294 A | 11/1990 | Salama | 600/30 |
| 5,010,925 A | 4/1991 | Atkinson et al. | 137/847 |
| 5,052,594 A * | 10/1991 | Sorby | 222/490 |
| 5,064,416 A | 11/1991 | Newgard et al. | 604/167 |
| 5,105,848 A | 4/1992 | Kallenbach | 137/493.1 |
| 5,141,498 A | 8/1992 | Christian | 604/167 |
| 5,261,459 A | 11/1993 | Atkinson et al. | 137/846 |
| 5,269,763 A | 12/1993 | Boehmer et al. | 604/167 |
| 5,269,771 A | 12/1993 | Thomas et al. | 604/213 |
| 5,301,707 A | 4/1994 | Hofsteenge | 137/12 |
| 5,306,226 A | 4/1994 | Salama | 600/29 |
| 5,324,270 A | 6/1994 | Kayan et al. | 604/167 |
| 5,395,352 A | 3/1995 | Penny | 604/256 |
| 5,402,982 A | 4/1995 | Atkinson et al. | 251/149.1 |
| 5,403,293 A | 4/1995 | Grabenkort | 604/256 |
| 5,409,146 A | 4/1995 | Hazard et al. | 222/321.8 |
| 5,411,491 A | 5/1995 | Goldhardt et al. | 604/247 |
| 5,429,620 A * | 7/1995 | Davis | 604/538 |
| 5,443,452 A | 8/1995 | Hart et al. | 604/167 |
| 5,456,284 A | 10/1995 | Ryan et al. | 137/522 |
| 5,474,099 A | 12/1995 | Boehmer et al. | 137/15 |
| 5,496,280 A | 3/1996 | Vandenbroek et al. | 604/167 |
| 5,501,426 A | 3/1996 | Atkinson et al. | 251/149.1 |
| 5,513,659 A | 5/1996 | Buuck et al. | |
| 5,514,098 A | 5/1996 | Pfoslgraf et al. | 604/167 |
| 5,533,708 A | 7/1996 | Atkinson et al. | 251/149.1 |
| 5,540,661 A | 7/1996 | Tomisaka et al. | 604/265 |
| 5,624,395 A | 4/1997 | Mikhail et al. | |
| 5,634,877 A | 6/1997 | Salama | 600/29 |
| 5,693,001 A | 12/1997 | Salama | 600/290 |
| 5,707,357 A | 1/1998 | Mikhail et al. | 604/96 |
| 5,709,664 A | 1/1998 | Vandenbroek et al. | 604/167 |
| 5,727,770 A | 3/1998 | Dennis | 251/149.1 |
| 5,800,339 A | 9/1998 | Salama | 600/29 |
| 5,803,919 A | 9/1998 | Hart et al. | 604/167 |
| 5,893,826 A | 4/1999 | Salama | 600/31 |
| 5,924,452 A | 7/1999 | Szpara et al. | 137/846 |
| 6,024,729 A | 2/2000 | Dehdashtian et al. | 604/256 |
| 6,044,859 A * | 4/2000 | Davis | 137/15.19 |
| 6,050,934 A | 4/2000 | Mikhail et al. | 600/30 |
| 6,063,063 A | 5/2000 | Harboe et al. | 604/256 |
| 6,063,119 A | 5/2000 | Pintauro et al. | 623/12 |
| 6,071,266 A | 6/2000 | Kelley | 604/265 |
| 6,105,580 A | 8/2000 | Von Iderstein et al. | 128/885 |
| 6,119,045 A | 9/2000 | Bolmsjo | 607/156 |
| 6,162,196 A | 12/2000 | Hart et al. | 604/167 |
| 6,167,886 B1 | 1/2001 | Engel et al. | 128/885 |
| 6,183,413 B1 | 2/2001 | Migachyov | 600/29 |
| 6,767,340 B1 * | 7/2004 | Willis et al. | 604/256 |
| 2001/0054448 A1* | 12/2001 | McFarland | 137/849 |
| 2002/0170557 A1* | 11/2002 | Schmidt | 128/200.23 |

* cited by examiner

URINARY FLOW CONTROL VALVE

The present application claims the filing benefit of co-pending Provisional Application U.S. Serial No. 60/303,694 filed Jul. 6, 2001, the disclosure of which is hereby incorporated herein by reference in its entirety.

FIELD OF THE INVENTION

The present invention relates generally to urinary flow control valves, and, more particularly, to such valves adapted to allow discharge of urine by manual actuation thereof.

BACKGROUND OF THE INVENTION

Urinary control devices, such as urinary catheters, have been developed to facilitate bladder drainage in individuals who are unable to initiate or control such drainage for a variety of medical reasons. Two types of urinary catheters have been developed to assist in this need and can be considered as comprising either a continuous drainage catheter or a valved urinary catheter. Continuous drainage catheters are used when continuous drainage of an individual's bladder into a collection bag or reservoir is desired, such as during or after surgery or when mobility of the individual is not a primary concern. Valved urinary catheters, on the other hand, are used to retain urine within the bladder until the individual desires to void the bladder through actuation of a manual urinary flow control valve located within or external to the urethra. The urinary valves of such devices typically includes a valve housing with flexible, resilient walls that contain therewithin the actual valve member. When the housing walls are squeezed, the walls flex and cause the valve therein to deform and open for release of urine. Release of the squeezing pressure on the housing walls allows the valve to return to its original, closed state.

Valved urinary catheters are used predominantly with mobile individuals so as to provide a urinary flow control device that is not discernable by others and that is compatible with the individual's normal daily activities. However, the urinary valves used in such devices suffer from several shortcomings and drawbacks. For example, the valves may be susceptible to unintended opening and undesirable urine leakage due to movement of the individual. Additionally, current urinary valves are not believed to work reliably across the broad range of urethral pressures typically encountered by the valves during normal use. Thus, while some valves may have good closing characteristics at low pressures where urine is only beginning to build up behind the valve, those valves may leak under higher pressures as urine accumulates in the urethra. Other valves may stay closed well in the presence of high pressure, but may leak at the very low pressures encountered before there is a sufficient build-up of urine to keep the valve closed.

SUMMARY OF THE INVENTION

The present invention provides manually actuatable urinary valves which overcome the foregoing shortcomings and drawbacks. To this end, and in accordance with the principles of the present invention, a urinary valve is provided in the form of a double-duckbill valve which deforms to open, and restores to the closed position when released. The double-duckbill valve is advantageously mounted within a valve housing so as to deform when the valve housing walls are squeezed. The double-duckbill bill comprises a pair of intersecting duckbill-like structures oriented perpendicular to each other so as to present a cruciform shape. Each duckbill has a pair of inclined lips or walls that extend from the base of the valve and converge at a pair of intersecting apexes at an inlet end of the valve. The inlet end is advantageously positioned to face upstream towards the urine flow from the bladder.

The double duckbill valve is advantageously slit along only a single axis, i.e, along the apex of only one of the duckbill-like structures. The effect is to have a single duckbill valve with structure perpendicular thereto that is "hollow" like a duckbill valve, but is unslit. The unslit lips thus form a pair of wedge-shaped supports integral with but perpendicular to the slit lips to stiffen the lips or walls of the slit lips to thereby improve the fluid seal. The fluid seal is further improved by an elastomeric band that is retained within a groove formed around the exterior of the valve and positioned slightly inwardly of the juncture of the duckbill walls with the valve base. The band at least partially overlies the converging walls of the intersecting double duckbills near their juncture with the valve base. The elastomeric band pre-loads or biases the valve (along with any fluid pressure at the inlet end of the valve) to a normally closed position.

The double-duckbill valve design of the present invention advantageously provides a reliable closure or seal at both high and low urethral pressures, as well as across the range of pressures normal encountered therebetween.

Typical of prior manually actuated urinary valves is that they are coupled directly to the valve housing so that squeezing the valve housing wall would cause the valve therewithin to deform and open. One disadvantage of such a design is that movement of the user could translate to inadvertent opening of the valve. To this end, and in accordance with another aspect of the present invention, a urinary valve, such as but not necessarily the double-duckbill valve of the present invention, is positioned within the valve housing, but in spaced relationship from the flexible walls of the valve housing so that the valve is not necessarily actuated merely by some flexing of the housing walls, but by flexing of the housing walls sufficiently to reach and then impact or bear against the valve to thereby deform same. The result is to isolate the valve from the housing walls.

The urinary valve may be isolated from the valve housing walls by a member that holds the valve away from the housing walls while tending to resist transfer of forces to the valve from the housing wall. Advantageously, the isolating member is flexible so as to resist transferring such forces. In one embodiment, the isolating member is a stem extending from the valve housing wall and connected to the urinary valve. Where the double-duckbill valve is used, the stem may be tubular and attached to the valve base to allow urine to flow through the stem to the valve while supporting the valve in non-contact relationship within the valve housing so that a clearance is established between the walls of the valve housing and the valve. The isolation member mechanically isolates the valve from forces applied to the valve housing and/or to any discharge tube extending therefrom during normal movement that are not intended to open the valve. The isolation member also provides a flexible support for the valve within the valve housing such that minor distortions of the valve housing do not accidently actuate the valve to an open position.

In accordance with yet another aspect of the present invention, several "crush limiting" components are provided to form positive stops as a user pinches the valve housing and actuates the valve to an open position. These components limit overactuation of the valve and stop valve deflection at an optimal opening distance to prevent restricted fluid flow.

By virtue of the foregoing, there are thus provided manually actuatable urinary valve structures which overcome drawbacks and shortcomings previously encountered with manually actuatable urinary valves. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE DRAWINGS

Figure 1:
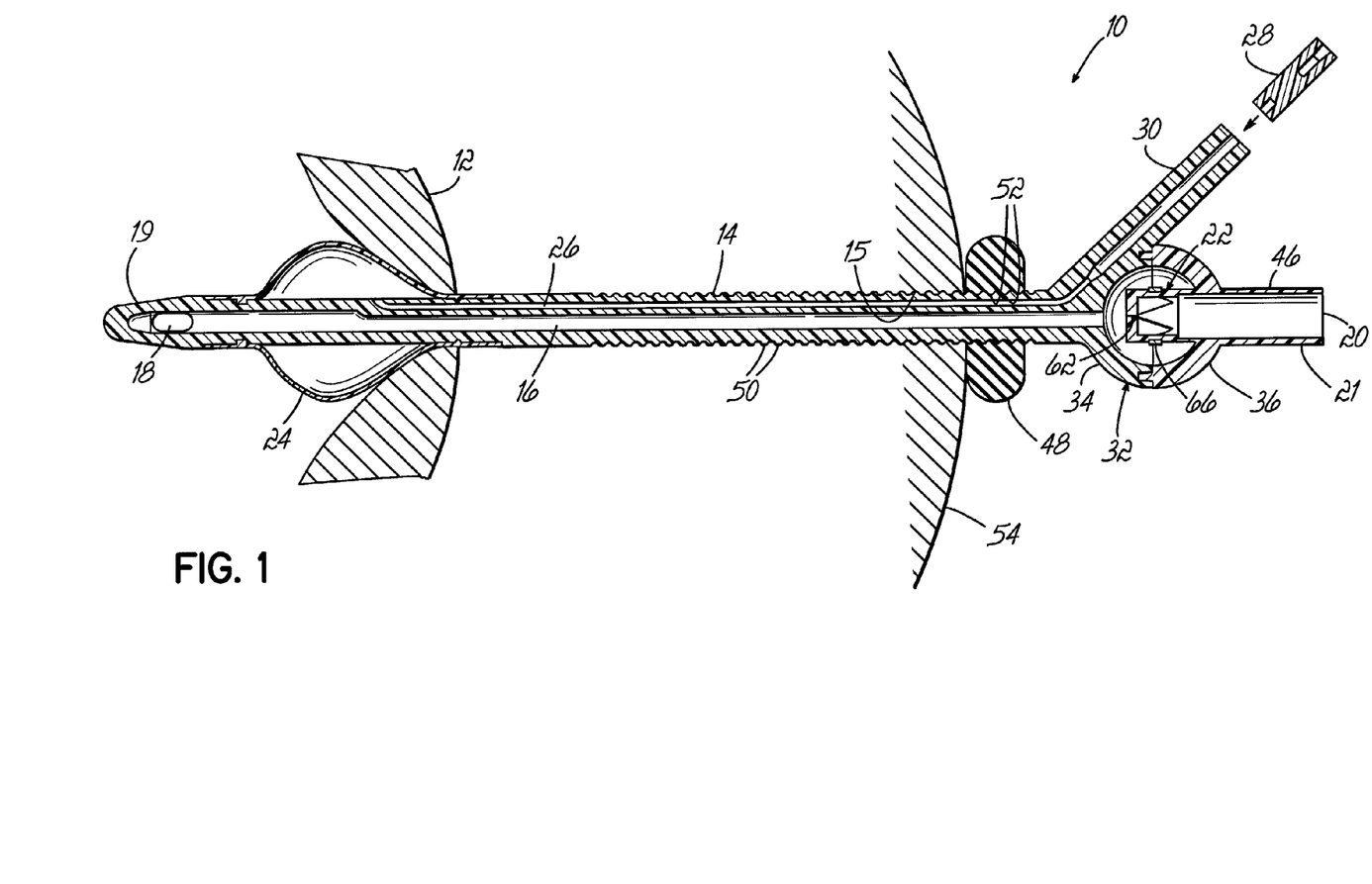
FIG. 1 is a cross-sectional view of a urinary catheter in operational position for draining a bladder and having a urinary flow control valve in accordance with the principles of the present invention.
Figure 2:
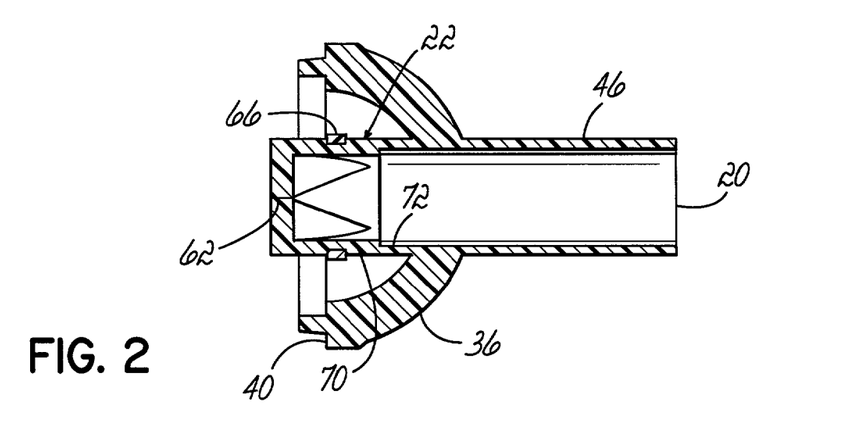
FIG. 2 is an enlarged side elevational view, partially in cross-section, of the urinary flow control valve of FIG. 1.

With reference to FIG. 1 there is shown a urinary catheter 10 for purposes of describing an embodiment of urinary flow control valve 22 in accordance with the principles of the present invention. Catheter 10 is shown by way of example and not limitation. To this end, catheter 10 is shown in operational position for controlling flow of urine from a bladder 12 by manual manipulation of valve 22 as will be hereinafter described.

Urinary catheter 10 has an elongated catheter shaft 14 that is adapted to be inserted through a patient's urethra (such as at 15) so as to provide a urine discharge passageway 16 extending from a pair of opposite inlets 18 (one shown) located within the bladder 12 at the distal end 19 of the catheter 10 and communicating via valve 22 to a urine discharge outlet 20 located outside the urethra at the proximal end 21 of the catheter 10. Urinary catheter 10 is formed, such as by injection molding, extrusion or transfer molding processes, from silicone, such as 40 or 50 durometer liquid silicone rubber, supplied by GE-Bayer Silicones of Waterford, New York under the name Baysilone LSR 4040 and LSR 4050.

Further referring to FIG. 1, an inflatable balloon 24 is provided on the catheter shaft 14 for seating and sealing the urinary catheter 10 in the bladder 12 as is well known in the art. An inflation lumen or passageway 26 is provided in the wall of the catheter shaft 14 that fluidly communicates with the balloon 24 mounted on the catheter shaft 14 and a microvalve 28 mounted within a microvalve extension arm 30 of the urinary catheter 10. A needle (not shown) or other device is inserted through the microvalve 28 to inflate the balloon 24 with fluid as shown in FIG. 1 to seat and seal the catheter 10 in the bladder 12.

In the embodiment of the invention shown herein, the valve 22 is supported within a spherical valve housing 32 connected to the catheter shaft 14 at proximal end 21 thereof. The valve housing 32 includes a pair of hemispherical bodies or walls 34 and 36 that are joined along abutting outer annular edges 38 and 40 (FIG. 6), respectively, to form the spherical valve housing 32. Hemispherical body or wall 34 is integral with the catheter shaft 14 and includes a groove 42 (FIG. 6) formed in the annular edge 38. The valve 22 is held with the hemispherical body 36 having an annular rib 44 (FIG. 6) formed on the annular edge 40 that is received in the groove 42. A urinary discharge tube 46 is integral with the hemispherical body 36 and defines the urine discharge outlet 20 at a remote end of the urinary catheter 10. In use, urine flows from the bladder 12 through the catheter shaft 14, through the valve 22 and out through the discharge tube 46 upon manual actuation of the valve 22 as will be described in detail below.

A silicone anchoring collar 48 (FIG. 1) is provided around the catheter shaft 14 outwardly of the balloon 24 and frictionally engages the outer surface of the catheter shaft 14 to hold the walls of the balloon 24 in sealing contact with bladder orifice and neck as shown in FIG. 1. Rounded serrations 50 are provided along the outside of the catheter shaft 14 and register with serrations 52 on the inside face of the collar 48. The serrations 50 and 52 serve to hold the collar 48 in place which, in turn, holds the balloon seal in place to prevent leakage around the catheter shaft 14. In the female, the collar 48 presses against the body 54 around the opening to the urethra. The design, structure and operation of the components of catheter 10, with the exception of valve 22 and/or its relationship to valve housing 32, may be conventional such as are shown in U.S. Pat. Nos. 4,968,294;

5,306,226; and 5,800,339, all assigned to the assignee hereof and the disclosures of which, in their entireties, are incorporated as if set out fully herein.

Figure 3:
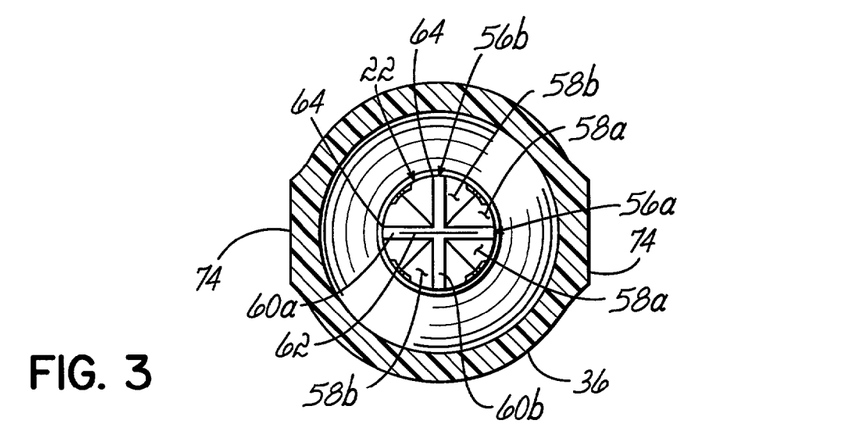
FIG. 3 is an enlarged front elevational view of the valve illustrated in FIG. 2 in an unactuated state with an inlet orifice of the valve in a closed position.

In accordance with one aspect of the present invention, the valve 22 comprises a double-duckbill valve in fluid communication with the urine discharge passageway 16. The double-duckbill valve 22 has a pair of duckbill-like structures 56a and 56b (see FIGS. 3 and 5) oriented perpendicular to each other so as to present a cruciform shape. Each duckbill-like structure 56a and 56b (FIG. 5) has a pair of inclined lips or walls 58a and 58b, respectively, that converge at a pair of intersecting apexes 60a and 60b, respectively, at an inlet end of the valve 22. The inlet end of the valve 22 faces upstream toward the urine flow from the bladder 12.

The double-duckbill valve 22 is advantageously slit along only a single axis, i.e, along the apex 60a of duckbill-like structure 56a to form a single slit 62. The duckbill-like structure 56b is unslit. The slit 62 defines an inlet orifice to the valve 22 that is operable to control urine flow through the urinary catheter 10 from the bladder 12. The unslit duckbill-like structure 56b defines a pair of wedge-shaped hollow supports 64 (FIG. 5) that are each integral with but perpendicular to one of the converging walls 58a of the slit duckbill-like structure 56a. The wedge-shaped supports 64 stiffen the lips or walls 58a of the slit duckbill-like structure 56a to resist opening of the slit 62 and thereby improve the fluid seal.

Figures 5, 9:
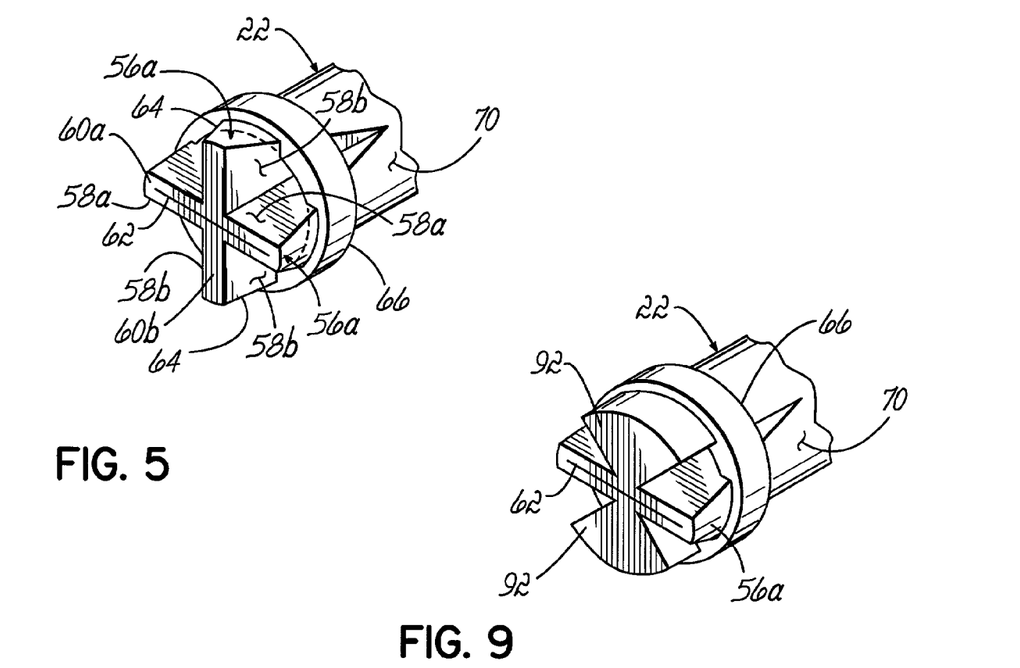
FIG. 5 is an enlarged partial perspective view of the urinary flow control valve of FIG. 1 illustrating an elastomeric band disposed about the valve to urge the inlet orifice to the closed position.
FIG. 9 is a view similar to FIG. 5 showing a yet further alternative embodiment of urinary flow control valve in accordance with the principles of the present invention.

As shown in FIG. 5, the fluid seal may be further improved by an elastomeric band 66 that is retained within a groove 68 (FIG. 6) formed around the exterior of the valve 22 and positioned slightly inwardly of the juncture of the duckbill walls 58a and 58b with a base 70 of the valve 22. The band 66 at least partially overlies the converging walls 58a and 58b of the intersecting duckbill-like structures 56a and 56b near their juncture with the valve base 70. The elastomeric band 66 pre-loads or biases the valve 22 (along with any fluid pressure at the inlet end of the valve 22) to a normally closed position as shown in FIG. 5. The elastomere band 66 is formed from silicone, such as 60 durometer silicone rubber, supplied by Wacker Silicones Corporation of Adrian, Michigan. In an alternative embodiment, the groove 68 is dispensed with and an annular shoulder (not shown) is provided around the exterior of the valve 22 so as to position the band 66 slightly inwardly of the juncture of the duckbill walls 58a and 58b with the base 70 of the valve 22 when the band 66 is positioned around the valve 22 and placed in abutting relationship with the annular shoulder (not shown). Alternatively, the band 66 is positioned around the valve 22 and bonded to the valve 22 through adhesive or other suitable methods of bonding so as to be positioned slightly inwardly of the juncture of the duckbill walls 58a and 58b with the base 70 of the valve 22 without the use of the groove 68 or the annular shoulder (not shown).

In accordance with another aspect of the present invention, a urinary flow control valve, such as double-duckbill valve 22, is positioned in spaced relationship from the flexible walls of the valve housing 32 through an isolation member such as a flexible tubular stem 72 extending from the hemispherical body 36 and connected to the valve base 70. The tubular stem 72 supports the valve 22 in non-contact relationship within the valve housing 32 so that a clearance is established between the spherical walls of the valve housing 32 and the valve 22. The tubular stem 72 has a sufficiently thin wall, for example a wall thickness of about 0.020 in., to mechanically isolate the valve 22 from forces applied to either the valve housing 32 or the discharge tube 46 during normal movement that are not intended to open the valve 22. The tubular stem 72 also provides a flexible support for the valve 22 within the valve housing 32 such that minor distortions of the valve housing 32 do not accidently actuate the valve 22 to an open position as described in detail below. The tubular stem 72 is coupled between the double-duckbill valve 22 and the discharge outlet 20 of the discharge tube 46 so as to allow urine to flow through the stem 72 to the discharge outlet 20. Alternative isolation members may be utilized as will be apparent to those skilled in the art. By way of example, and not limitation, the isolation member could be a different thin, flexible member such as a diaphragm or wall (not shown) extending between a wall 34 or 36 of the valve housing 32 and the urinary control flow valve (which could be a valve as shown, for example in the aforementioned patents, or double-duckbill valve 22 by way of example, or other valve structure as will be readily apparent to those ordinarily skilled in the art) which diaphragm or wall, like isolation stem 72, resists transfer of forces from walls 34, 36 to valve 22.

Figure 4:
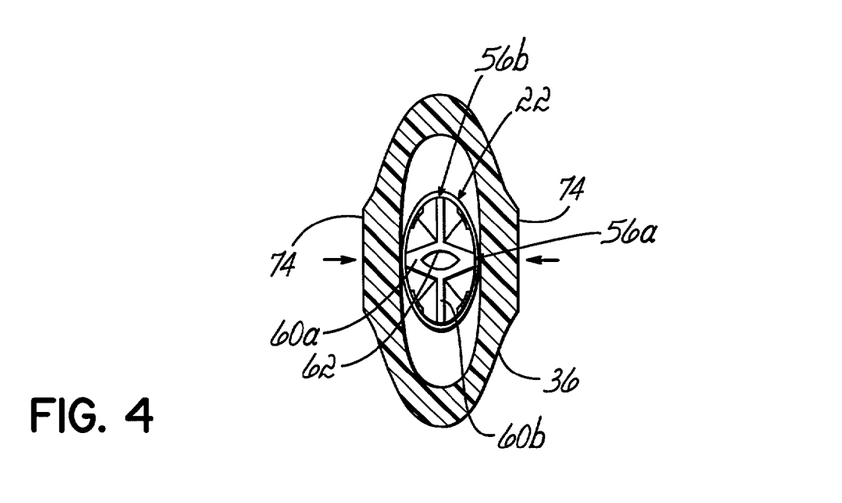
FIG. 4 is a view similar to FIG. 3 illustrating the valve in an actuated state with the inlet orifice of the valve in an open position to permit drainage of urine through the urinary catheter of FIG. 1.

When a crushing force is applied to the walls 34 and/or 36 of valve housing 32 along the axis of the slit 62 of duckbill-like structure 56a, i.e., the user squeezes the valve housing 32 with fingers at opposite finger pads 74 (FIG. 3), the cruciform structure of the double-duckbill valve 22 is deformed sufficiently to compress the valve 22 along the axis of the slit 62 such that the lips or walls 58a come apart and open the valve 22 for the flow of urine as shown in FIG. 4 (i.e., through passageway 16, into valve housing 32, through valve 22, and out through stem 72 and outlet 20). The valve 22 is actuated only when the wall 36, for example, of the valve housing 32 deforms sufficiently to move into position to impact and bear against valve 22 to thereby apply a sufficient crushing force to the double-duckbill valve 22 to open the slit 62. After the crushing force is removed, the natural tendency of the walls 58a is to close back up to close the slit 62. The perpendicular wedge-shaped supports 64 and the elastomeric band 66 help assure closure, and also retain the walls 58a in a closed position to seal the slit 62 when there is only low fluid pressure, such as when urine first begins to collect up around the OD of the valve 22. Alternatively, valve 22 may be formed integrally with wall 36 so as not to be isolated therefrom by stem 72, for example, such that squeezing pressure on housing 32 may cause valve 22 to deform without having to move into contact with valve 22 as that contact is inherent in the integral attachment (not shown). However, the isolation of valve 22 is considered advantageous to reduce the likelihood that valve 22 will be unintentionally opened due to typical movement of valve housing 32 as the patient moves about during normal activities.

The valve 22 is oriented in the valve housing 32 so that fluid flows in only one direction upon external actuation of the valve housing 32, thereby permitting fluid flow from the inlet end of the valve 22 at the apexes 60a and 60b of the cruciform toward the outlet end of the valve 22 at the connection of the tubular stem 72 with the valve base 70. Otherwise, the valve 22 is designed to remain closed in the presence of fluid pressure at the inlet end of the valve 22.

Figure 6:
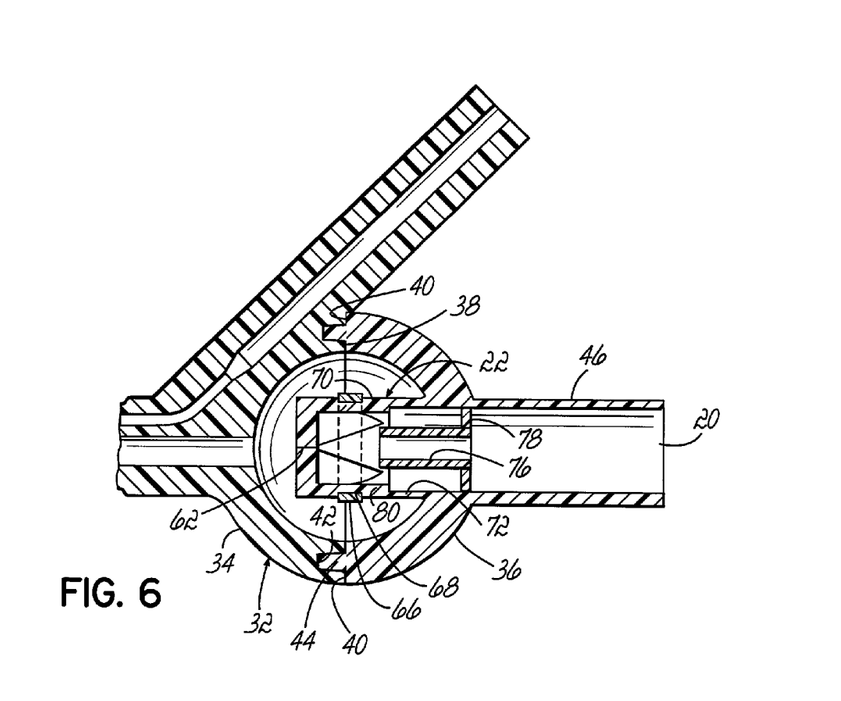
FIG. 6 is an enlarged partial cross-sectional view illustrating an alternative embodiment of the urinary flow control valve of FIG. 1 with a first crush limiting structure in accordance with further principles of the present invention.
Figure 6A:
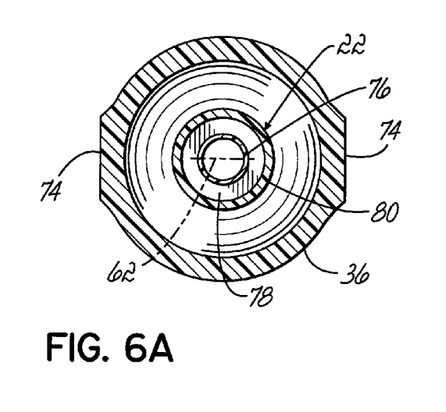
FIG. 6A is an enlarged front elevational view of the valve of FIG. 6 in a closed position.
Figure 6B:
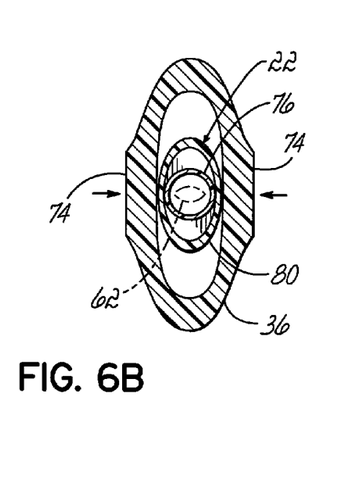
FIG. 6B is a view similar to FIG. 6A illustrating the valve of FIG. 6 in an open position.

Several "crush limiting" components may be provided to form positive stops as a user pinches the valve housing 32 and actuates the valve 22 to the open position. These components are intended to limit overactuation of the valve 22 which may result in restricted fluid flow, such as through catheter 10, and stop valve deflection at an optimal opening distance. In accordance with one aspect of the present invention as shown in FIGS. 6, 6A and 6B, a rigid or semi-rigid shell or tube 76 is suspended within the valve 22 through an annular flexible flange 78. The tube 76 has an outer diameter (OD) that is less than an inner diameter (ID) of the valve 22, and the OD dimension of the tube 76 is selected to stop valve deflection at an optimal opening position of the slit 62. Valve deflection stops when a wall 80 of the valve 22 engages the tube 76 as shown FIG. 6B.

Figure 7:
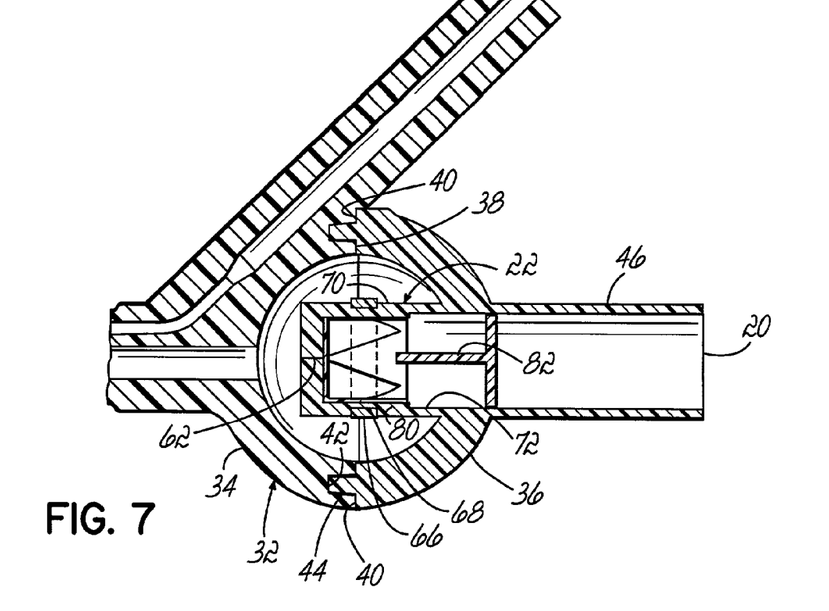
FIG. 7 is an enlarged partial cross-sectional view illustrating a further alternative embodiment of the urinary flow control valve of FIG. 1 with a second crush limiting structure in accordance with further principles of the present invention.
Figures 7A, 7B:
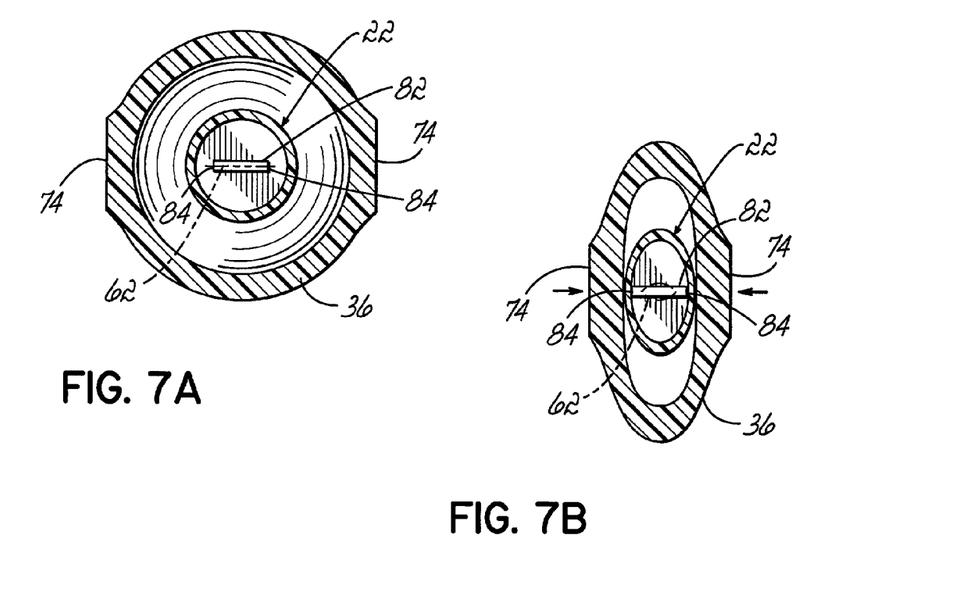
FIG. 7A is an enlarged front elevational view of the valve of FIG. 7 in a closed position.
FIG. 7B is a view similar to FIG. 7A illustrating the valve of FIG. 7 in an open position.

According to another aspect of the present invention, as shown in FIGS. 7, 7A and 7B, a rigid or semi-rigid blade 82 is suspended within the valve 22 and oriented parallel to the axis of the slit 62. The width of the blade 82 is selected to stop valve deflection at the optimal opening of the slit 62 whereat the wall 80 of valve 22 engages lateral edges 84 of the blade 82 as shown in FIG. 7B.

Figure 8:
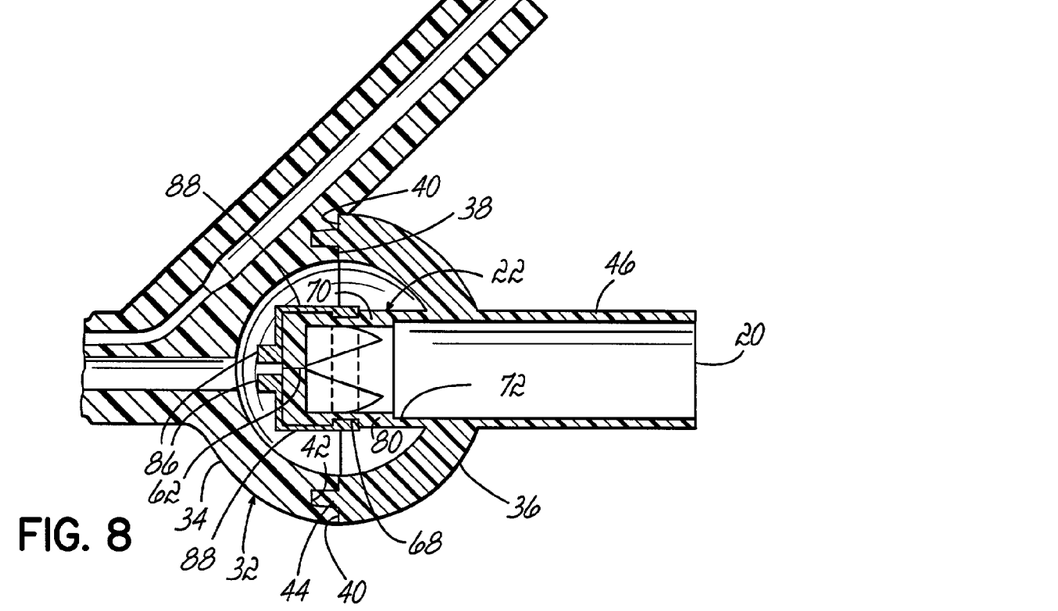
FIG. 8 is an enlarged partial cross-sectional view illustrating a still further alternative embodiment of the urinary flow control valve of FIG. 1 with a third crush limiting structure in accordance with further principles of the present invention.
Figures 8A, 8B:
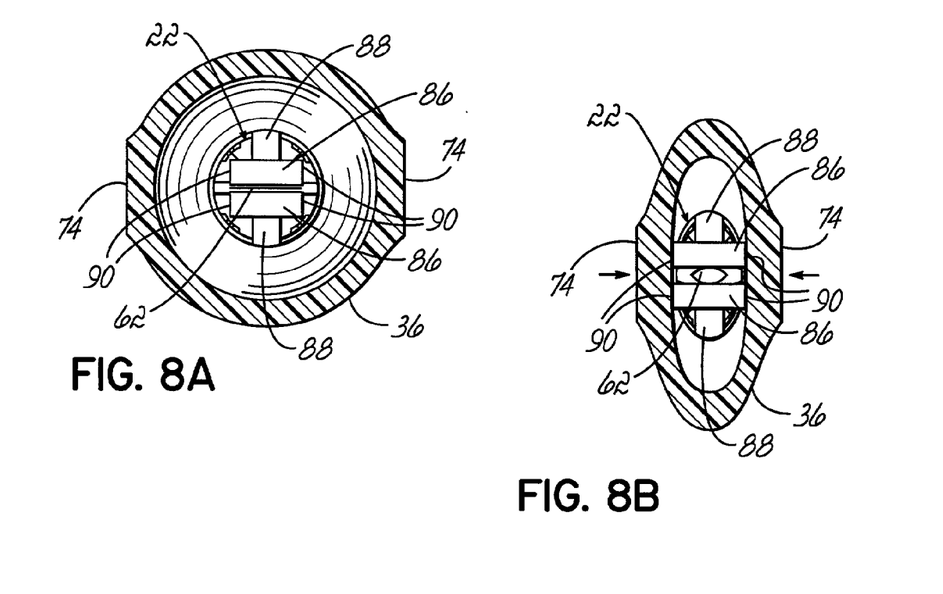
FIG. 8A is an enlarged front elevational view of the valve of FIG. 8 in a closed position.
FIG. 8B is a view similar to FIG. 8A illustrating the valve of FIG. 8 in an open position.

Alternatively, as shown in FIGS. 8, 8A and 8B, a pair of rigid or semi-rigid stop elements 86 are positioned external to the valve 22 and supported or suspended in place by flexible fingers 88 such the stop elements 86 limit valve deflection perpendicular to the slit 62 to the optimal opening distance while flexing outwardly to allow the valve 22 to open. In one embodiment of the present invention, the stop elements 86 comprise a pair of rectangular plates suspended on opposite sides of the slit 62, although other structural shapes of the stop elements 86 are possible as well. Each stop element 86 has a width selected to stop valve deflection at the optimal opening position of the slit 62 whereat the ID of valve housing 32 engages lateral edges 90 of the stop elements 86 as shown in FIG. 8B.

In accordance with yet another aspect of the present invention, as shown in FIG. 9, stop elements 92 in the form of rigid or semirigid wedge-shaped supports are provided that are each integral with but perpendicular to respective ones of the converging walls 58a of the slit duckbill-like structure 56a. The solid wedge-shaped supports 92 provide a limit to the opening of the valve 22, while also limiting the crushing of valve housing 32 during actuation, so as to provide the optimal opening position of the slit 62. Inserts of metal or other materials (not shown) may be molded within the supports 92 to control the outward flexing extent of the supports 92 to obtain the optimal opening position of the slit 62.

While valve 22 is shown with catheter 10, it will be appreciated that urinary flow control valve 22 and isolating a valve from the valve housing both provide various advantages and benefits, either singly or in combination, by which to reduce the likelihood of inadvertent opening of the valve during normal activities, the ability to remain closed under a range of normally encountered urethral pressures, and also the avoidance of overactuation which may result in restricted urine flow.

In use, the urinary flow control valve 22 is associated with a urethra 15, such as by being inserted into urethra 15, or by being fluidically coupled to the urethra such as by a fluid passageway, which may be a urinary catheter 10. When it is appropriate to empty the patient of urine, the patient simply squeezes wall 36, for example, of housing 32 until valve 22 opens, while avoiding overactuation if crush limiting structure is provided, such that urine flows out of discharge outlet 20. The patient then releases the valve housing 32 which allows valve 22 to reclose and begin the process of allowing urine to again collect up behind the valve 22, but without concern from inadvertent leakage.

By virtue of the foregoing, there are thus provided urinary flow control valves which overcome drawbacks and disadvantages associated with prior urinary flow control valves.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, while the urinary valve 22 and housing 32 are shown herein as being external to urethra 15, depending upon the relative size of the urethra and valve housing, the valve(s) of the present invention could also be used within the urethra, provided the valve can be activated manually such as by palpation of the body surrounding the urethra. Moreover, while the urinary valves of the present invention are shown at the terminal end of a urethral catheter, the valves could be used along a length of catheter, without a catheter extending into the bladder such as with a shorter artificial passageway 16 extending into the urethra but not all the way to the bladder, and/or with no such passageway at all, depending upon the placement of the valve. Additionally, while the isolation member and crush limiting structure are shown herein in connection with a urinary flow control valve, the concepts may be applicable to other flow control valves. The invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. A urinary flow control valve comprising:
   a double-duckbill valve adapted to fluidly communicate with a urine discharge passageway, said double-duckbill valve having:
   an orifice operable to control urine flow therethrough;
   a first duckbill structure having a first pair of inclined walls terminating at a first apex; and
   a second duckbill structure oriented perpendicular to said first duckbill structure and having a second pair of inclined walls terminating at a second apex;
   each of said first and second duckbill structures being generally hollow;
   said orifice comprising a single slit formed in, and extending generally in the direction of, only one of said first and second apexes.

2. The urinary flow control valve of claim 1 further comprising an elastomeric band disposed about said double-duckbill valve and operable to urge said orifice to a closed position.

3. The urinary flow control valve of claim 1 further comprising:
   a valve housing defined by at least one wall; and
   an isolation member extending from said wall to said double-duckbill valve, said double-duckbill valve being supported in said valve housing in spaced relationship with said wall by said isolation member.

4. The urinary flow control valve of claim 3, said isolation member being a stem.

5. The urinary flow control valve of claim 4, said stem being flexible.

6. The urinary flow control valve of claim 3, said isolation member being a tubular stem.

7. The urinary flow control valve of claim 6, said tubular stem being coupled with said double-duckbill valve so as to allow urine to flow through said stem.

8. The urinary flow control valve of claim 7, said valve housing having a discharge outlet, the tubular stem being coupled between said discharge outlet and said double-duckbill valve.

9. The urinary flow control valve of claim 6, said tubular stem being flexible.

10. The urinary flow control valve of claim 1 further comprising:
a valve housing containing said double-duckbill valve;
said valve housing having a discharge outlet operatively coupled with said double-duckbill valve.

11. The urinary flow control valve of claim 1 further comprising a crush limiting member associated with said double-duckbill valve.

12. The urinary flow control valve of claim 11, said crush limiting member including a blade member disposed within said double-duckbill valve.

13. The urinary flow control valve of claim 3 wherein said valve housing is flexible and is defined by at least one flexible wall.

14. A flow control valve comprising:
a valve member having a normally closed orifice;
an elastomeric band disposed about said valve member and operable to urge said orifice to a closed position;
a flexible valve housing defined by at least one flexible wall; and
an isolation member extending from said wall to said valve member, said valve member being supported in said valve housing in spaced relationship with said wall by said isolation member so as to be actuatable.

15. The flow control valve of claim 14 wherein said valve member has a groove associate therewith, the elastomeric band being a separate component and situated in said groove.

16. The flow control valve of claim 14 wherein said valve member has a base and at least a pair of inclined walls extending from said base at respective junctures of said inclined walls with said base, said band being positioned inwardly of said junctures of said inclined walls with said base.

17. The flow control valve of claim 14, said isolation member being a stem.

18. The flow control valve of claim 17, said stem being flexible.

19. The flow control valve of claim 14, said isolation member being a tubular stem.

20. The flow control valve of claim 19, said tubular stem being coupled with said valve member so as to allow fluid to flow through said stem.

21. The flow control valve of claim 19, said tubular stem being flexible.

22. The flow control valve of claim 14 further comprising a crush limiting member associated with said valve member.

23. The flow control valve of claim 22, said crush limiting member including a blade member disposed within said valve member.

24. The flow control valve of claim 14, said orifice being defined by a single slit.

25. The flow control valve of claim 14, said valve member being a double-duckbill valve.

26. A flow control valve comprising:
a valve member having a normally closed orifice;
a valve housing; and
an isolation member extending between said valve housing and said valve member whereby to support said valve member in spaced relationship to said valve housing, said isolation member supporting said valve member so as to resist accidental actuation of said valve member;
said isolation member being a stem.

27. The flow control valve of claim 26, said stem being flexible.

28. The flow control valve of claim 26, said stem being tubular.

29. The flow control valve of claim 28, said tubular stem being coupled with said valve member so as to allow fluid to flow through said stem.

30. The flow control valve of claim 28, said tubular stem being flexible.

31. The flow control valve of claim 26 further comprising a crush limiting member associated with said valve member.

32. The flow control valve of claim 31, said crush limiting member including a blade member disposed within said valve member.

33. The flow control valve of claim 26, said orifice being defined by a single slit.

34. The flow control valve of claim 26, said valve member being a double-duckbill valve.

35. The flow control valve of claim 26 wherein said valve member is contained within said valve housing.

36. A urinary catheter comprising:
a urine discharge passageway;
a urinary flow control valve associated with said urine discharge passageway;
said urinary flow control valve being a double-duckbill valve;
said double-duckbill valve having:
an orifice operable to control urine flow therethrough;
a first duckbill structure having a first pair of inclined walls terminating at a first apex; and
a second duckbill structure oriented perpendicular to said first duckbill structure and having a second pair of inclined walls terminating at a second apex;
each of said first and second duckbill structures being generally hollow;
said orifice comprising a single slit formed in, and extending generally in the direction of, only one of said first and second apexes.

37. The urinary catheter of claim 36 further comprising an elastomeric band disposed about said double-duckbill valve and operable to urge said orifice to a closed position.

38. The urinary catheter of claim 36 further comprising:
a valve housing defined by at least one wall; and
an isolation member extending from said wall to said double-duckbill valve, said double-duckbill valve being supported in said valve housing in spaced relationship with said wall by said isolation member.

39. The urinary catheter of claim 30, further comprising a crush limiting member associated with said double-duckbill valve.

40. A urinary flow control valve comprising:
a double-duckbill valve adapted to fluidly communicate with a urine discharge passageway, said double-duckbill valve having:
an orifice operable to control urine flow therethrough;
a first duckbill structure terminating at a first apex; and
a second duckbill structure oriented perpendicular to said first duckbill structure and terminating at a second apex;
said orifice comprising a single slit formed in, and extending generally in the direction of, only one of said first and second apexes; and an elastomeric band disposed about said double-duckbill valve and operable to urge said orifice to a closed position.

41. The urinary flow control valve of claim 40 further comprising:
a valve housing defined by at least one wall; and
an isolation member extending from said wall to said double-duckbill valve, said double-duckbill valve being supported in said valve housing in spaced relationship with said wall by said isolation member.

42. The urinary flow control valve of claim 41, said isolation member being a stem.

43. The urinary flow control valve of claim 42, said stem being flexible.

44. The urinary flow control valve of claim 41, said isolation member being a tubular stem.

45. The urinary flow control valve of claim 44, said tubular stem being coupled with said double-duckbill valve so as to allow urine to flow through said stem.

46. The urinary flow control valve of claim 45, said valve housing having a discharge outlet, the tubular stem being coupled between said discharge outlet and said double-duckbill valve.

47. The urinary flow control valve of claim 44, said tubular stem being flexible.

48. The urinary flow control valve of claim 40 further comprising:
a valve housing containing said double-duckbill valve;
said valve housing having a discharge outlet operatively coupled with said double-duckbill valve.

49. The urinary flow control valve of claim 40 further comprising a crush limiting member associated with said double-duckbill valve.

50. The urinary flow control valve of claim 49, said crush limiting member including a blade member disposed within said double-duckbill valve.

51. The urinary flow control valve of claim 41 wherein said valve housing is flexible and is defined by at least one flexible wall.

52. A urinary catheter comprising:
a urine discharge passageway;
a urinary flow control valve associated with said urine discharge passageway;
said urinal flow control valve being a double-duckbill valve;
said double-duckbill valve having:
an orifice operable to control urine flow therethrough;
a first duckbill structure having a first pair of inclined walls terminating at a first apex;
a second duckbill structure oriented perpendicular to said first duckbill structure and having a second pair of inclined walls terminating at a second apex;
said orifice comprising a single slit formed in, and extending generally in the direction of, only one of said first and second apexes; and
an elastomeric band disposed about said double-duckbill valve and operable to urge said orifice to a closed position.

53. The urinary catheter of claim 52 further comprising:
a valve housing defined by at least one wall; and
an isolating member extending from said wall to said double-duckbill valve, said double-duckbill valve being supported in said valve housing in spaced relationship with said wall by said isolating member.

54. The urinary catheter of claim 53, said isolation member being a stem.

55. The urinary catheter of claim 54, said stem being flexible.

56. The urinary catheter of claim 53, said isolation member being a tubular stem.

57. The urinary catheter of claim 56, said tubular stem being coupled with said double-duckbill valve so as to allow urine to flow through said stem.

58. The urinary catheter of claim 57, said valve housing having a discharge outlet, the tubular stem being coupled between said discharge outlet and said double-duckbill valve.

59. The urinary catheter of claim 56, said tubular stem being flexible.

60. The urinary catheter of claim 52 further comprising:
a valve housing containing said double-duckbill valve;
said valve housing having a discharge outlet operatively coupled with said double-duckbill valve.

61. The urinary catheter of claim 52 further comprising a crush limiting member associated with said double-duckbill valve.

62. The urinary catheter of claim 61, said crush limiting member including a blade member disposed within said double-duckbill valve.

63. The urinary catheter of claim 53 wherein said valve housing is flexible and is defined by at least one flexible wall.

64. A urinary catheter comprising:
a urine discharge passageway;
a urinary flow control valve associated with said urine discharge passageway;
said urinary flow control valve being a double-duckbill valve;
said double-duckbill valve having an orifice operable to control urine flow therethrough;
a valve housing defined by at least one wall; and
an isolation member extending from said wall to said double-duckbill valve, said double-duckbill valve being supported in said valve housing in spaced relationship with said wall by said isolation member, said isolation member supporting said double-duckbill valve so as to resist accidental actuation of said double-duckbill valve.

65. The urinary catheter of claim 64, the double-duckbill valve having:
a first duckbill structure having a first pair of inclined walls terminating at a first apex; and
a second duckbill structure oriented perpendicular to said first duckbill structure and having a second pair of inclined walls terminating at a second apex;
said orifice comprising a single slit formed in, and extending generally in the direction of, only one of said first and second apexes.

66. The urinary catheter of claim 64, said isolation member being a stem.

67. The urinary catheter of claim 66, said stem being flexible.

68. The urinary catheter of claim 64, said isolation member being a tubular stem.

69. The urinary catheter of claim 68, said tubular stem being coupled with said double-duckbill valve so as to allow urine to flow through said stem.

70. The urinary catheter of claim 69, said valve housing having a discharge outlet, the tubular stem being coupled between said discharge outlet and said double-duckbill valve.

71. The urinary catheter of claim 68, said tubular stem being flexible.

72. The urinary catheter of claim 64 further comprising a crush limiting member associated with said double-duckbill valve.

73. The urinary catheter of claim 72, said crush limiting member including a blade member disposed within said double-duckbill valve.

74. A urinary catheter, comprising:
a urine discharge passageway;
a valve member associated with said urine discharge passageway and having a normally closed orifice operable to control urine flow therethrough;
a valve housing defined by at least one wall; and
an isolation member extending from said wall to said valve member, said valve member being supported in said valve housing in spaced relationship with said wall by said isolation member, said isolation member supporting said valve member so as to resist accidental actuation of said valve member.

75. The urinary catheter of claim 74, said isolation member being a stem.

76. The urinary catheter of claim 75, said stem being flexible.

77. The urinary catheter of claim 74, said isolation member being a tubular stem.

78. The urinary catheter of claim 77, said tubular stem being coupled with said valve member so as to allow urine to flow through said stem.

79. The urinary catheter of claim 78, said valve housing having a discharge outlet, the tubular stem being coupled between said discharge outlet and said valve member.

80. The urinary catheter of claim 77, said tubular stem being flexible.

81. The urinary catheter of claim 74 further comprising a crush limiting member associated with said valve member.

82. The urinary catheter of claim 81, said crush limiting member including a blade member disposed within said valve member.

83. The urinary catheter of claim 74 wherein said valve housing is flexible and is defined by at least one flexible wall.

84. A urinary flow control valve comprising:
a valve member adapted to fluidly communicate with a urine discharge passageway and having an orifice operable to control urine flow therethrough;
a flexible valve housing defined by at least one flexible wall; and
an isolation member extending from said wall to said valve member, said valve member being supported in said valve housing in spaced relationship with said wail by said isolation member so as to be actuatable.

85. The urinary flow control valve of claim 84, said isolation member being a stem.

86. The urinary flow control valve of claim 85, said stem being flexible.

87. The urinary flow control valve of claim 84, said isolation member being a tubular stem.

88. The urinary flow control valve of claim 87, said tubular stem being coupled with said valve member so as to allow urine to flow through said stem.

89. The urinary flow control valve of claim 88, said valve housing having a discharge outlet, the tubular stem being coupled between said discharge outlet and said valve member.

90. The urinary flow control valve of claim 87, said tubular stem being flexible.

91. The urinary flow control valve of claim 84 further comprising a crush limiting member associated with said valve member.

92. The urinary flow control valve of claim 91, said crush limiting member including a blade member disposed within said valve member.

* * * * *

UNITED STATES PATENT AND TRADEMARK OFFICE
CERTIFICATE OF CORRECTION

| | |
|---|---|
| PATENT NO. | : 7,037,303 B2 |
| APPLICATION NO. | : 10/000276 |
| DATED | : May 2, 2006 |
| INVENTOR(S) | : Spencer W. Beaufore et al. |

It is certified that error appears in the above-identified patent and that said Letters Patent is hereby corrected as shown below:

Column 1
Lines approximately 31-32, "valves of such devices typically includes a" should be -- valves of such devices typically include a --.

Column 2
Line approximately 27, "pressures normal encountered therebetween." should be --pressures normally encountered therebetween. --

Column 7
Line approximately 8, "as shown FIG. 6B." should be -- as shown in FIG. 6B. --.

Line approximately 19, "such the stop elements 86 limit valve deflection.." should be -- such that stop elements 86 limit valve deflection --

Column 9
Line 32 (Claim 15), "member has a groove associate therewith," should be -- member has a groove associated therewith, --

Column 10
Line 52 (Claim 39), "The urinary catheter of claim 30" should be -- The urinary catheter of claim 36 --

Column 11
Line 44 (Claim 52), "said urinal flow control valve being" should be -- said urinary flow control valve being --

UNITED STATES PATENT AND TRADEMARK OFFICE
CERTIFICATE OF CORRECTION

| | | |
|---|---|---|
| PATENT NO. | : 7,037,303 B2 | |
| APPLICATION NO. | : 10/000276 | |
| DATED | : May 2, 2006 | |
| INVENTOR(S) | : Spencer W. Beaufore et al. | |

It is certified that error appears in the above-identified patent and that said Letters Patent is hereby corrected as shown below:

Column 14
Line 12 (Claim 84), "spaced relationship with said wail" should be -- spaced relationship with said wall --

Signed and Sealed this

Twenty-second Day of August, 2006

JON W. DUDAS
*Director of the United States Patent and Trademark Office*